United States Patent [19]

Theoharides

[11] Patent Number: 5,250,529

[45] Date of Patent: Oct. 5, 1993

[54] METHOD ALLEVIATING MIGRAINE HEADACHE WITH MAST CELL DEGRANULATION BLOCKING AGENTS

[75] Inventor: Theoharis C. Theoharides, Brooklhne, Mass.

[73] Assignee: KOS Pharmaceuticals, Inc., Miami, Fla.

[21] Appl. No.: 815,124

[22] Filed: Dec. 27, 1991

Related U.S. Application Data

[63] Continuation-in-part of Ser. No. 478,164, Feb. 8, 1990, abandoned.

[51] Int. Cl.5 .............. A61K 31/495; A61K 31/41; A61K 31/35; A61K 31/21; A61K 31/13; A61K 31/135
[52] U.S. Cl. .................... 514/255; 514/263; 514/381; 514/457; 514/510; 514/579; 514/650
[58] Field of Search ............. 514/263, 255, 557, 381, 514/579, 650, 510, 457

[56] References Cited

U.S. PATENT DOCUMENTS

| | | | |
|---|---|---|---|
| 4,599,359 | 7/1986 | Cooper | 514/557 |
| 4,794,112 | 12/1988 | Cooper | 514/255 |
| 4,829,064 | 5/1989 | Sunshine et al. | 514/255 |

OTHER PUBLICATIONS

International Search Report, Application No. PCT/US92/11227, including following references: W. Split, et al., "Ketotifen in the Treatment of Chronic Cluster Headache," *Headache*, 24:147-149, vol. 3, May 1984.
W. Split, et al., "Ketotifen (Zaditen) in the Therapy of Cluster Headache," *Rev. Roum. Med.* 1983, 21(3), pp. 253-256.
W. Split, et al., "Neurologia", *Neurol. Neurochir. Pol.*, vol. 18, No. 2, 1984, pp. 105-109.
C. I. Parodi, et al., "Terfenadine Prophylaxis in Migraine", *Acch. Psicol. Neurol. Psichiatr.*, vol. 49, No. 3, pp. 299-303.
W. D. Singer, "Pharmacological Management of Posttraumatic Headaches", *J. Head Traum. Rehabil.*, vol. 4, No. 1, 1989, pp. 83-86.
*Merck Index*, 11th Edition, #4771, p. 645, Hydroxyzine (1983).
*Current Therapy*, "Headache" pp. 788-793 (1981).
Tek, Deniz, "The Effectiveness of Nalbuphine and Hydroxyzine for Emergency Treatment of Severe Headache", *Annals of Emer. Med.* Mar. 1987, pp. 107-112.

*Primary Examiner*—Frederick E. Waddell
*Assistant Examiner*—K. Weddington
*Attorney, Agent, or Firm*—Foley & Lardner

[57] ABSTRACT

A method of preventing or alleviating a migraine headache which comprises administering a pharmaceutically effective amount of a mast cell degranulation blocking agent just prior to or during the prodromal phase of the migraine in the absence of an analgesic. The agent can also be administered in combination with a central nervous system stimulant.

17 Claims, No Drawings

METHOD ALLEVIATING MIGRAINE HEADACHE WITH MAST CELL DEGRANULATION BLOCKING AGENTS

CROSS-REFERENCE TO RELATED APPLICATION

This application is a continuation-in-part of U.S. Ser. No. 07/478,164, filed Feb. 8, 1990, now abandoned, which is hereby incorporated in its entirety by reference.

BACKGROUND OF THE INVENTION

The present invention relates to a method of alleviating or preventing a migraine headache through the administration of a mast cell degranulation blocking agent.

A) Migraines

Migraine headaches are known to produce the most intense headache reported, which are comparable to that of a brain aneurysm rupture. As many as 15% of all people, especially in industrialized societies, are sufferers, with an estimated yearly cost due to treatment and work lost in the United States of America alone of almost one billion dollars. Prior to the present invention, there has been no effective way to prevent the last minute onset of the migraine headache.

The pathophysiology of migraine headaches involves vasoconstriction (the closing or tightening of arteries, which reduces blood flow) and vasodilation (the opening of the vessels to increase blood flow). It appears that a variety of stimuli, such as intense light, noise, anxiety, exertion, cold, heat, hormones, food additives and certain foods, result in constriction of extracranial vessels. The vasoconstriction is followed by a sequential or reflex powerful vasodilation, which subsequently spreads to intracranial vessels. It is during this phase that a patient feels an intense, throbbing headache. Increased levels of norepinephrine, serotonin, bradykinin and substance P, as well as products of tissue anoxia are considered to be the endogenous pain producing molecules accompanied by direct sensory nerve stimulation, because of stretching due to vasoconstriction and vasodilation.

The phases of a migraine headache have been separated into the prodrome, aura and acute painful headache stages. The prodrome is the primary stage of a migraine attack characterized by an alteration of mood, energy or passive functions. This stage can occur for hours before the onset of the headache. The mood alterations include euphoria, loquaciousness, unprovoked apathy, depression, inertia, drowsiness, irritability, repetitive yawning, aggression and heightened sensitivity to various levels of sound (sonophobia). Nausea and vomiting, as well as paresthesias in the extremities, may also accompany these symptoms.

The aura or second stage has been defined by the onset of fear of light (photophobia) and visual disturbances brought on by a reduction of cerebral blood flow due to vasospasm.

The headache phase is vascular with distension and increased pulsation of cranial arteries. Increased vascular permeability is associated with the release of peptides, especially bradykinin and substance P, as well as molecules such as histamine and serotonin, which cause local pain when they reach perivascular nerve endings.

Migraine headaches develop suddenly, and reach maximal intensity very quickly, in contrast to ordinary muscular headaches, which develop gradually and rarely, if ever, reach a severity comparable to that of migraine headaches. Patients suffering from migraine headaches are often so well aware of the pain that will ensue from an impending migraine that they become apprehensive and frightened. As a result of this anxiety, the patients hyperventilate and/or tense their neck muscles. Both of these effects usually lead to a muscle tension headache. In other words, the mere anticipation and fear of an impending migraine headache brings about an ordinary muscular headache in virtually all migraine patients. The patients can thus suffer from two different types of affliction simultaneously.

B) Mast cells and migraines

Mast cells are normal components of the connective tissue and play an important role in allergy and inflammation. These cells are localized in the gastrointestinal mucosa, skin and lung. It is believed that mast cells are so located because these tissues are the main entry points for infective organisms and allergens—chemicals which trigger the body's immune response. Recently, mast cells have been shown to be located at strategic points around capillaries and small blood vessels, especially in the brain, where they are important in regulating the extent of constriction or dilatation of vessels critical in migraines.

Each mast cell contains up to 500 secretory granules, each storing more than 20 potent biological compounds. Mast cells secrete the contents of these granules, i.e., degranulate, when triggered by various specific and non-specific mechanisms. Degranulation is defined as the release of any or all mediators from any or all secretory granules, whether in parallel, differentially or selectively.

The degranulation of mast cells in response to various agents is a biological consequence of the activation of one or more receptors which are located on the surface of the mast cell. The best known receptor is immunoglobulin E (IgE), which is involved in allergic reactions—the only well-understood pathological process involving mast cells to date. In the reaction, IgE binds strongly to mast cells through its Fc receptor. When mast cell-bound IgE reacts with an antigen, the latter bridges two or more IgE and causes mast cell degranulation with subsequent release of mediators, either stored or synthesized during mast cell degranulation.

There is also evidence that neurotransmitters such as acetylcholine and neuropeptides, all of which are molecules released from neurons in the nervous system, and female sex hormones, such as estradiol and progesterone, may also trigger mast cell degranulation through specific receptors, especially in response to stress. Other known triggers include viruses, bacterial toxins, drugs, such as aspirin, morphine and curare, contrast media used in radiology, extreme heat, cold, solar radiation, hyperosmotic media and pressure. It is, therefore, clearly important to block mast cell degranulation in response to these stimuli.

The compounds released by the mast cells following degranulation are known to cause many biological processes which are part of the overall response of the body to invasion by infective organisms (inflammatory response) or allergens. Examples of such processes are vasoconstriction or vasodilation, and inflammation.

Compounds released by mast cell degranulation which may be associated with migraines include: histamine, kinins, prostaglandin $E_2$ and vasoactive intestinal peptide, which are vasodilatory, as well as serotonin, prostaglandin $F_{2\alpha}$ and leukotrienes, which are vasoconstrictive. In addition, histamine, kinins, prostaglandins and serotonin can cause pain directly.

Histamine and the other mediators are secreted from the granules of mast cells during degranulation of mast cells due to activation of specific surface receptors. The histamine and other mediators then bind to specific receptors on the surface of endothelial cells on vessels, neurons or other tissues. Vasodilation and chemoattraction permits lymphocytes to leave the circulation and enter the tissue, where they cause additional mast cell degranulation and other responses. The process of degranulation continues, eventually involving many mast cells.

Mast cell degranulation thus contributes to the symptoms experienced by migraineurs during the aural and acute headache phase of the disease.

C) Treatment

A variety of pharmacological agents has been employed in the prior art in attempting to treat individuals suffering from migraine headaches. The pharmacological agents previously used generally counteracted the symptoms of a migraine after, rather than before, occurrence of the acute migraine headache phase, specifically by antagonizing the effects of serotonin or its utilization at the brain stem and forebrain synapses.

Examples of symptomatic treatments suggested by the prior art include use of extracranial vasoconstrictors, typically ergot alkaloids such as ergotamine, and sumatriptan. In addition, it was reported that the vasoconstrictor sumatriptan has been reported to be effective in the treatment of migraine by inhibiting the release of serotonin by the nerve cells in the brain (Moskowitz et al., "Evidence that Serotonin$_1$-like Heteroreceptors Block Neuropeptide Release and Neurogenic Plasma Extravasation to Mediate the Actions of Ergot Alkaloid and Sumatriptan (GR43175) in Migraine Headaches," XVth International Symposium on Cerebral Blood Flow and Metabolism, BRAIN-91, Abstract 14 (Jun. 1-6, 1991)). However, if vasoconstrictors or serotonin agonists are taken before the migraine, they may precipitate the migraine, and they are contraindicated in coronary heart disease and in pregnancy.

Chronic prophylactic administration of certain drugs has been tried using 5-hydroxytryptamine (5-HT, serotonin) antagonists such as methysergide and cyproheptadine, vasodilators such as papaverine, beta-adrenergic blockers, such as propranolol, nadolol, timolol or atenolol; tricyclic anti-depressants, such as amitriptyline; calcium channel antagonists, such as nifedipine and verapamil, and phenothiazines, such as meclizine or phenelzine. Certain of these drugs, however, have severe side effects. For example, propranolol and nifedipine inhibit the function of the heart, and while the former causes impotence, the latter can precipitate a headache. Amitriptyline casues a drop in blood pressure, sedation, behavioral changes and weight gain.

Anti-histamines have been used in combination with analgesics (narcotic and/or non-narcotic). In particular, anti-histamines have been used in the treatment of migraines after the onset of pain, in combination with a narcotic analgesic. The use of antihistamines in this manner was considered desirable because they are sedating, they may reduce nausea, and they may potentiate the action of analgesics, while minimizing their side-effects, especially hypotension. They have not been reported to have any direct action on their own against migraine pain in the form and method they have been used to date.

For example, meperidine hydrochloride (Demerol ®) has been used in combination with the anti-histamine hydroxyzine (in the form of hydroxyzine pamoate). Hydroxyzine has been thought to limit some of the undesirable side actions of meperidine, such as hypotension and anaphylaxis, and to potentiate the effect of the opioid.

The effectiveness of hydroxyzine per se in the symptomatic treatment of migraines was questioned in a recent study. In Tek et al., *The Effectiveness of Nalbuphine and Hydroxyzine for the Emergency Treatment of Severe Headache*, Annals of Emergency Medicine 16: 308-313 (March, 1987), it was concluded that intramuscular administration of nalbuphine or hydroxyzine (50 mg) or a combination of the two during severe migraine is no more effective than a placebo in the treatment of pain associated with classic migraine. However, in this study, the migraine pain was treated well after occurrence of the acute headache phase. Moreover, the dosage of hydroxyzine used by Tek was 50 mg per patient, the normal dose used in combination with a narcotic analgesic.

Although not reported in the literature, high doses of hydroxyzine (over 100 mg) alone have been used on an ad hoc basis for the symptomatic treatment of migraine headaches after the pain has occurred despite the fact that hydroxyzine used alone in smaller doses (50 mg) had been reported (e.g., by Tek et al.) to be ineffective in the treatment of migraine.

In Wild, U.S. Pat. No. 4,017,614, the antihistamine buclizine was administered with an analgesic after the onset of the aura. Buclizine was, however, indicated to be ineffective if administered individually, and at high doses was reported to trigger a headache.

Opioid analgesics, such as morphine, are known to make the migraine worse, as are high doses of non-opioid analgesics, such as aspirin, ibuprofen, acetaminophen and the like. This undesirable effect is found with all analgesics. Concurrent administration of high doses of analgesics along with certain antihistamines can also trigger rather than inhibit mast cell degranulation (see, e.g., Wojnar et al., J. Allergy Clin. Immunol., vol. 66, No. 1, pp. 37-45 (July 1980); Masini et al., Agents and Actions, vol. 18, ½ (1986), pp. 85-88). The deleterious effects of high dosages of analgesics is known in the literature (see, e.g., Goth, A., *Effects of drugs on mast cells*, Adv. Pharmacol. 5:47-78 (1967)).

SUMMARY OF THE INVENTION

It is an object of the present invention to provide a method of preventing or alleviating migraine headaches that can be carried out prior to or during the prodrome phase.

Another object of the present invention is to provide a method that avoids undesirable chronic prophylactic administration.

In accomplishing the foregoing objectives, there has been provided, in accordance with one aspect of the present invention, a method of preventing or all ®Viating a migraine headache which comprises the step of administering to a patient a -pharmaceutically effective amount of a mast cell degranulation blocking agent just prior to or during the prodrome phase in the absence of an analgesic administered prior to the onset of the acute migraine phase.

In a preferred embodiment, the mast cell degranulation blocking agent is hydroxyzine.

In another preferred embodiment, the mast cell degranulation blocking agent is administered in combination with a pharmaceutically effective amount of a central nervous system stimulant such as caffeine, which also permits better absorption.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

DETAILED DESCRIPTION OF THE PREFERRED EMBODIMENTS

The method of the present invention prevents or alleviates the migraine headache by inhibiting the release from mast cells of the vasoactive (i.e., vasoconstrictive and vasodilatory) and nociceptive compounds which are involved in the precipitation of the migraine. It has been found that administration of mast cell blocking agents, especially those which interfere with the cell receptor activation mechanisms in the primary prodromal stage, will prevent or alleviate the onset of the two later stages in the migraine process.

By "prevention or alleviation" is meant the following: assuming that the fully developed migraine headache is associated with the activation of a specific number of mast cells, the development thereof can involve sequential activation of a certain percentage of this total at a time. If the mast cell degranulation blocking agent is administered to the patient before the beginning of the activation process, the result will be prevention of the migraine. However, if the blocking agent is administered during the activation process, but before all of the necessary mast cells are activated, then the result will be alleviation of the migraine. In other words, since all of the necessary mast cells will not be activated, the full migraine headache will not develop and the resulting pain, which has yet to develop, will be less severe than would be the case if the blocking agent were not administered. The reduction in severity of the impending migraine headache constitutes "alleviation" of the migraine.

Particularly preferred are certain histamine-1 receptor antagonists, antihormones and polyamines, especially those specific compounds set forth below. As to the H-1 receptor antagonists, even more especially preferred are azelastine, azatadine, hydroxyzine and ketotifen, based on their potency in inhibiting cranial mast cell secretion as distinct from mast cells present elsewhere in the body. A particularly suitable mast cell degranulation blocking agent is hydroxyzine and the pharmaceutically acceptable, non-toxic salts of hydroxyzine.

Some of the classes of drugs which inhibit mast cell degranulation and examples of such classes are the following:
Anthralinic acid derivatives
   N-(3,4-dimethoxycinnamoyl) anthranilic acids
Antibiotics
   Chlorotetracycline
   Cyclosporin A
   Tetracyclic pyridone-2-carboxylic acid
Antihormones which are estrogen or progestin receptor antagonists
   Estrogen receptor antagonists
      Clomiphene
      Tamoxifen
   Progestin receptor antagonists
      Mifepristone
Arachidonic acid metabolites
   Leukotriene $D_4$
   Lipoxin B
   Phospholipase $A_2$
   Prostaglandin $D_2$
   Prostaglandin $E_1$
   Prostaglandin $E_2$
ATPase inhibitors
   Ethancrynic acid
   Ouabain
   Quercetin
Calcium entry blockers
   Diltiazem
   Nifedipine
   Nimodipine
   Verapamil
2'-Carboxylatochromon-5'-yl-2-hydroxypropanederivatives
   Bis(acetoxymethyl) cromoglycate
   Disodium cromoglycate
   Nedocromil
Central nervous system stimulants
   Methyl Xanthines:
      3-Isobutyl-1-methylxanthine
      Aminophylline
      Caffeine
      Enprophylline
      Theophylline
Histamine-1 receptor antagonists containing ring structure
   Piperidines
      Azelastine
      Azatadine
      Burfroline
      Cyproheptadine
      Doxantrozole
      Forskolin
      Ketotifen
      Lodoxamide trimethamine
      Loperamide
      Myricetin
      Oxatomide
      Pizotifen
      Proxicromil
      Terfenadine
   Piperazines
      1-(5-Isoquinolinylsulfonyl)-2-methylpiperazine
      1-(1-Hydroxy-5-isoquinolinylsulfonyl)piperazine
      Cetirizine
      Etodroxizine
      Hydroxyzine
      N-(optionally substituted benhydryl)-N'-(optionally substituted)piperazines
   Tertiary Alkylamines
      Pyrilamine
Peptides
   L-Asp-Ser-Asp-Pro-Arg Forssman antibody
Interleukin-1 receptor antagonist
Lymphocyte Inhibitory Factor (LIF)
Substance P-receptor antagonist
Phenothiazines
  Chlorocyclazine
  Prochlorperazine
  Promethazine
  Thioridazine
  Trifluoroperazine
Polyamines
  Putrescine
  Spermidine
  Spermine
Proteoglycans
  Heparin
Quinoline derivatives
  1,3-oxazolo[4,5-h]quinolines
  2-Carboxypyrimidoquinolines
  3-Aminoquinolines
Steroids
  Cortisone
  Danocrine
  Dexamethasone
  Diethylstilbestrol
  Prednisone
  Testosterone
Thiophene derivatives
  1-Methyl-2(1,3,4-oxadiazol-2(3H)-one-5-yl)
  Benzimidazole
Toxins
  Diphtheria toxin
  Pertussis toxin
Tricyclic antidepressants
  Amitriptyline
  Doxepin
  Imipramine
Miscellaneous compounds
  2-Substituted 3-dimethylamino-5,6-methylenedioxydines
  2-o-Propoxyphenyl-8-azapurin-6-one
  2-Ethoxyethyl-5-chloro-benzoxazole-2-carboxylate
  5-Amino-4-imidazolecarboxyamide riboside
  5-Chlorobenzoxazole-2-carboxcylic acid
  7-Methyl-5-propyl-s-triazole[1,5c]pyrimidine-2-amine
  7-(2-Hydroxyethoxy)-9-oxoxanthene-2-carboxylic acid
  9-Chloro-5-oxo-7-(1H-tetrazol-5yl)-5H-[1]benzopyrano [2,3-b]pyridine sodium salt pentahydrate
  Amiloride
  Cloxacepride
  Deoxycoformycin
  Dipyridamole
  Fistein
  Flufenamic acid
  Nylidrin hydrochloride
  p-Bromophenacyl bromide
  Pimozide
  Salbutamol sulfate Particularly useful known mast cell degranulation blocking agents are certain anti-histamines (H1-receptor antagonists) such as hydroxyzine, azelastine, azatadine, cetirizine, cyproheptadine, ketotifen, oxatomide and terfenadine. H1-receptor antagonists are defined as having "affinity" (i.e., binding tightly) to the histamine-1 receptor at concentrations of $5 \times 10^{-5}$ M or lower.

All the members of the foregoing classes may not necessarily inhibit mast cell degranulation. However, the ability of any individual members to inhibit mast cell degranulation can be determined by the test set forth below.

First, mast cells from rats (peritoneal cavity) or humans (chronic peritoneal dialysis fluid) are purified; otherwise, rat basophilic leukemia (RBL) cells are kept in culture. Any of these mast cells are then exposed to various concentrations of inhibitory compounds to allow binding of the inhibitor to the receptor sites before testing their efficacy with respect to inhibition of mast cell degranulation. They are then used as such or washed free of unbound drug before exposure to stimuli known to induce degranulation. Compounds which are inhibitory prevent the stimulus from causing degranulation by binding to specific receptors or inactivating a crucial step in the degranulation process.

It is important to note that some $H_1$-receptor antagonists actually cause mast cell degranulation and thus must be avoided (see Pini et al., *Degranulation of Rat Mesentery Mast Cells by Antihistamines: Influence of Ionization.* Agents and Actions, vol. 8/5: 491–96 (1978)). Examples are given in Table 1 below.

TABLE 1

| ANTI-HISTAMINES WHICH CAUSE MAST CELL DEGRANULATION | |
|---|---|
| Compound | $ED_{20}$ for Histamine Release |
| Clorphenyramine | $10^{-3}$ M |
| Cyclizine | $5 \times 10^{-4}$ M |
| Diphenhydramine | $10^{-3}$ M |
| Promethazine | $10^{-4}$ M |

$ED_{20}$ = effective dose causing 20% secretion.
M = molar concentration.

The mast cell degranulation inhibitor in the dosage administered preferably are capable of passing the blood-brain barrier in an effective amount. The ability of the mast cell degranulation blocking agent to pass the blood-brain barrier in effective amounts can be determined by calculating the percentage of a particular agent that reaches the brain when administered by a conventional route to experimental animals by methods known in the literature, especially utilizing radiolabeled agents.

The instant invention is predicated on the early and rapid inhibition of the mast cell degranulation process to prevent or alleviate the migraine headache. To effect this early intervention, dosage forms for the delivery of hydroxyzine necessitate those that achieve high blood levels of the drug very rapidly. These dosage forms are adapted for a variety of conventional routes of administration, including oral, parenteral and transepithelial, such as sublingual, or transmucosal, transdermal, intranasal and rectal.

The mast cell degranulation blocking agent is administered in a pharmaceutically effective amount. The dosage range for pharmaceutical effectiveness can be determined by reference to standard laboratory tests for inhibition of mast cell degranulation and by the dosages used for such agents in other conditions. The pharmaceutically effective dose of the mast cell degranulation blocking agent can be approximated by its $ID_{20}$, which is defined as the dose necessary to cause 20% inhibition in mast cells when applied to mast cells stimulated in vitro. The $ID_{20}$ of selected inhibitors of the anti-histamine category is as follows:

TABLE 2
ANTIHISTAMINES WHICH INHIBIT RAT MAST CELL DEGRANULATION IN VITRO

| Antihistamines | $ID_{20}$ for Histamine Release |
|---|---|
| Azatadine | $10^{-7}$ M |
| Cyproheptadine | $5 \times 10^{-6}$ M |
| Hydroxyzine | $5 \times 10^{-5}$ M |
| Ketotifen | $10^{-5}$ M |
| Oxatomide | $10^{-7}$ M |
| Terfenadine | $5 \times 10^{-6}$ M |

$ID_{20}$ = inhibitory dose causing 20% inhibition.
M = molar concentration.

The dosage of mast cell degranulation blocking agent for use in mammals can be calculated from the effective dose data by experimental selection. In general, the $ID_{20}$ is tested at 0.05 mg to 50 mg per kilogram body weight of the animal.

The mast cell degranulation blocking agent can be administered in the form of the active agent itself or as a pharmaceutically acceptable salt of the active agent. The term "pharmaceutically acceptable salt" means a non-toxic, substantially non-irritating salt of the compound used. Typical salts include those containing a cation which is an alkali metal or alkaline earth metal, such as sodium, potassium, calcium, magnesium or ammonium. Suitable cations for the salt include sulphate, Phosphate, tartrate and citrate. Other acceptable salts are those with non-toxic organic acids such as fatty acids of one to six carbon atoms.

Hydroxyzine is a preferred mast cell degranulation blocking agent because it also possesses other characteristics which are helpful in treating migraine. It is known to be a mild sedative, a tranquilizer, an anti-emetic and an inhibitor of neuronally-derived mast cell triggers. Finally, since hydroxyzine pamoate, a salt of hydroxyzine, is lipophilic, i.e. more soluble in lipid solvents than water, it allows chemicals, in this case hydroxyzine pamoate, to cross the vascular wall and the blood-brain barrier.

Hydroxyzine can be administered in dosages of about 0.1 to about ten (10) milligrams (mg) per kg or about 8 mg to about 800 mg for 80 kilograms (kg) of body weight of the subject per day. When the hydroxyzine is to be administered transmucosally, it is convenient to use hydroxyzine in the form of a pamoate salt.

Dosages per 80 kilograms bodyweight per day for several preferred blocking agents are given in Table 3 below.

TABLE 3
DOSAGES OF PREFERRED BLOCKING AGENTS

| Agent | Dosage(mg)/80 kg/day |
|---|---|
| Azatadine | 0.4–8 |
| Azelastine | 0.4–8 |
| Cyproheptadine | 0.4–40 |
| Hydroxyzine | 8–800 |
| Ketotifen | 0.2–50 |
| Oxatomide | 6–60 |
| Terfenadine | 6–400 |

The mast cell degranulation blocking agent can be administered by known methods for drug administration. The agents are typically administered as pharmaceutical compositions in combination with pharmaceutically acceptable carriers. Such compositions may be prepared from conventional materials by procedures well known in the art.

The compositions of this invention may be adapted for oral or parenteral administration, as well as for enteral administration orally or through mucus membranes such as intranasal, sublingual, buccal, rectal, as well as transdermal. A transdermal route is preferred for convenience, comfort, safety and avoidance of first pass metabolism.

Forms suitable for oral administration include tablets, dispersible powders, granules, capsules, syrups, elixirs and suspensions.

Compositions for oral use contain one or more conventional adjuvants, such as sweetening agents, flavoring agents, coloring agents and preserving agents, in order to provide a presentable and palatable preparation. Tablets may contain the active ingredients in a mixture with conventional pharmaceutically acceptable excipients. These include inert carriers, such as calcium carbonate, sodium carbonate, lactose, and talc; granulating and disintegrating agents, such as starch and alginic acid; binding agents such as starch, gelatin acacia; and, lubricating agents, such as magnesium stearate, stearic acid and talc. Tablets may be uncoated or coated by known techniques to delay disintegration and absorption in the gastrointestinal tract thereby providing a sustained action over a longer period of time. Similarly, suspensions, syrups and elixirs may contain active ingredients in mixture with any of the conventional excipients utilized in the preparation of such compositions. This includes suspending agents such as methylcellulose, tragacanth and sodium alginate; wetting agents such as lecithin, polyoxyethylene stearate or polyoxyethylene sorbidan monoleate; and preservatives. Capsules may contain the active ingredients alone or an admixture with an inert solid carrier, such as calcium carbonate, calcium phosphate or kaolin. These pharmaceutical compositions may contain up to 90% of active ingredients in combination with the carrier or adjuvant. Preferably, the compounds are put up in unit dosage forms particularly for oral administration. Such forms may contain the active ingredient separately, for example in separate layers. Oral administration is often preferred if the mast cell degranulation inhibiting agent is orally active. For patients who experience nausea or vomiting, sublingual administration is preferred.

The agents can be administered in sustained release form or in divided dosages.

In the case of mast cell degranulation inhibiting agents which are substantially destroyed or deactivated upon oral administration, or where a more immediate response is desired or prolonged duration of activity is desired, the mast cell degranulation blocking agents of this invention can also be administered transdermally or via other body membranes such as rectally, sublingually or buccally. Similarly, the compositions of this invention are administered by those routes with carriers known for such administration.

An advantage of the inventive method is that the use of the mast cell degranulation blocking agents as described does not involve a narrow therapeutic window in the sense that increasing the dosage leads to precipitation, rather than prevention/alleviation, of the migraine.

The mast cell degranulation blocking agent is administered without the concomitant administration of an effective amount of an analgesic. By the foregoing is meant that an analgesic is not administered just prior to or during the prodome when the mast cell degranulation blocking agent is first administered. Rather, the administration of an analgesic is deferred until later if and when the migraine pain actually occurs.

The term an "analgesic" refers to a substance known to exert an analgesic effect in standard laboratory test, typically the mouse hot plate test.

The mast cell degranulation blocking agent can be administered alone or in conjunction with other therapeutic agents, provided those therapeutic agents do not directly or indirectly promote mast cell degranulation. One preferred conjunct to the administration of a mast cell degranulation blocking agent is the administration of a xanthine-like central nervous system stimulant, for example, a methylxanthine such as caffeine. Such compounds are potent stimulants of the central nervous system. In particular, the use of a central nervous system stimulant such as caffeine results in vasoconstriction and adenosine receptor blocking action, which also reduces mast cell degranulation since the latter is augmented by adenosine which is released during anoxia. Caffeine also increases the absorption of drugs when co-administered.

These compounds also affect the actions of the heart, cause relaxation of bronchial smooth muscles and reduce the release of secretory products of a number of other endocrine and exocrine tissues. In addition, the caffeine counterbalances the sedative effect present with some of the mast cell degranulation blocking agents, which is particularly useful in patients who wish to maintain a normal life-style.

Besides caffeine, other xanthine compounds exerting a pattern of actions similar to that of caffeine, such as aminophylline, are also useful. (Although theophylline and theobromine can be used, their use is limited by their toxicity.)

The caffeine that can be administered with the mast cell degranulation blocking agent is administered in the pharmaceutically effective amount. A pharmaceutically effective amount denotes a dosage from 5 to 50 milligrams per kilogram body weight.

The following non-limiting examples further illustrate the invention.

EXAMPLE 1

Hydroxyzine Injection

A sterile solution of hydroxyzine hydrochloride, with sodium metabisulfate, in water for injection is provided in one (1.0) ml ampules containing 50 mg of hydroxyzine pamoate.

EXAMPLE 2

Tablets

Preferred embodiment for rapidly disintegrating tablets are as follows:

| Sublingual Tablet: | |
| --- | --- |
| Ingredients | mg/tablet |
| Hydroxyzine Pamoate | 50 mg |
| Milk sugar (12 mesh granular) | 25 mg |
| Starch | 20 mg |
| Talc | 8 mg |
| Magnesium Stearate | 0.4 mg |

EXAMPLE 3

Treatment

A female patient, age 29, with a ten-year history of migraine headaches occurring once every three months, not relieved during those ten years by a variety of narcotic and non-narcotic analgesics, and often related to her menstrual cycle, was administered sublingually hydroxyzine in the form of the pamoate ester. Her prodrome was characterized by nausea and photophobia and typically lasted roughly ½ hour. During the prodrome of the migraine, she took 50 mg hydroxyzine pamoate sublingually in the absence of any other analgesic. In each and every case, the migraine failed to appear as determined by the absence of severe headache and disappearance of nausea and photophobia. The patient was occasionally left with a mild, dull ache (i.e., a residual muscle tension headache) which was well tolerated.

EXAMPLE 4

Treatment

A female patient, age 26, with a four-year history of migraine headaches occurring at irregular intervals and unrelieved during those four years by narcotic or non-narcotic analgesics, was administered hydroxyzine in the form of the pamoate ester sublingually. Her prodrome was shown by generalized malaise and photophobia and sonophobia, i.e., intolerance to intense light or sound, respectively. Her prodrome typically lasted one to two hours. During the prodrome of the migraine, she took 50 mg of hydroxyzine pamoate powder in an inert carrier sublingually in the absence of any other analgesic. In each and every case, the migraine failed to appear as determined by the absence of severe headache and disappearance of photophobia and phonophobia. The patient was infrequently left with a dull ache (residual muscle tension headache) which was well tolerated.

What is claimed is:

1. A method of alleviating a migraine headache which comprises the step of administering to a patient a pharmaceutically effective amount of a mast cell degranulation blocking agent only during the prodrome phase in the absence of an analgesic administered prior to the onset of the acute migraine phase.

2. A method as claimed in claim 1, wherein said mast cell degranulation blocking agent is administered parenterally, orally, intranasally, sublingually, buccally, rectally or transdermally.

3. A method as claimed in claim 1, wherein said mast cell degranulation blocking agent is selected from the group consisting of mast cell degranulation blocking agents having histamine-1 receptor antagonist activity.

4. A method as claimed in claim 3, wherein said mast cell degranulation blocking agent is selected form the group consisting of azatadien, azelastine, cetirizine, cyproheptadien, doxantrozole, etodroxizine, forskolin, hydroxyzine, ketotifen, oxatomide and terfenadine.

5. A method as claimed in claim 4, wherein said mast cell degranulation blocking agent is hydroxyzine.

6. A method as claimed in claim 5, wherein said hydroxyzine is in the form of a pharmaceutically acceptable salt.

7. A method as claimed in claim 5, wherein said hydroxyzine is administered in an amount from about 0.05 to 50 milligrams per kilogram body weight of said patient.

8. A method as claimed in claim 7, wherein said hydroxyzine is administered in the form of hydroxyzine pamoate.

9. A method as claimed in claim 8, wherein said hydroxyzine pamoate is administered transmucosally.

10. A method as claimed in claim 1, wherein said mast cell degranulation blocking agent is a polyamine.

11. A method as claimed in claim 10, wherein said polyamine is spermine.

12. A method as claimed in claim 1, wherein said mast cell degranulation blocking agent is administered in conjunction with a pharmaceutically effective amount a central nervous system stimulant.

13. A method as claimed in claim 12, wherein said stimulant is caffeine.

14. A method as claimed in claim 4, wherein said mast cell degranulation blocking agent is ketotifen.

15. A method as claimed in claim 14, wherein said ketotifen is administered in an amount from about 0.005 to 0.5 milligrams per kilogram body weight of said patient.

16. A method as claimed in claim 1, wherein said mast cell degranulation blocking agent is the estrogen receptor antagonist tamoxifen.

17. A method as claimed in claim 1, wherein said mast cell degranulation blocking agent is the ATPase inhibitor quercetin.

* * * * *